US006936725B2

(12) United States Patent
Melzig et al.

(10) Patent No.: US 6,936,725 B2
(45) Date of Patent: Aug. 30, 2005

(54) PHOTOCHROMIC COMPOUNDS

(75) Inventors: Manfred Melzig, Wessling (DE); Herbert Zinner, Pentling (DE)

(73) Assignee: Rodenstock GmbH, Munich (DE)

( * ) Notice: Subject to any disclaimer, the term of this patent is extended or adjusted under 35 U.S.C. 154(b) by 804 days.

(21) Appl. No.: 09/819,705

(22) Filed: Mar. 29, 2001

(65) Prior Publication Data

US 2003/0045714 A1 Mar. 6, 2003

Related U.S. Application Data

(62) Division of application No. 09/259,053, filed on Mar. 1, 1999, now abandoned, which is a continuation of application No. 08/888,540, filed on Jul. 7, 1997, now abandoned, which is a continuation of application No. 08/573,583, filed as application No. PCT/DE94/00737 on Jun. 28, 1994, now abandoned.

(30) Foreign Application Priority Data

Jun. 28, 1993 (JP) ........................................ P43 21 487

(51) Int. Cl.[7] ............................................ C07D 491/04
(52) U.S. Cl. ...................................................... 549/384
(58) Field of Search .......................................... 549/384

(56) References Cited

U.S. PATENT DOCUMENTS

| | | | | |
|---|---|---|---|---|
| 3,567,605 | A | 3/1971 | Becker | 204/158 |
| 4,818,096 | A | 4/1989 | Heller et al. | 351/163 |
| 5,238,981 | A | 8/1993 | Knowles | 524/110 |
| 5,246,989 | A | 9/1993 | Iwamoto et al. | 524/89 |
| 5,451,344 | A | 9/1995 | Knowles et al. | 252/586 |
| 5,464,567 | A | 11/1995 | Knowles et al. | 252/586 |
| 5,527,911 | A | 6/1996 | Gugliemetti et al. | 544/250 |
| 5,840,926 | A | 11/1998 | Hughes | 549/384 |
| 5,847,168 | A | 12/1998 | Hughes | 549/384 |
| 6,106,744 | A | 8/2000 | Van Gemert et al. | 252/586 |

*Primary Examiner*—Deepak Rao
(74) *Attorney, Agent, or Firm*—Antonelli, Terry, Stout & Kraus, LLP

(57) ABSTRACT

A photochromic compound suitable for use as a single substance for photochromic tinting of a transparent plastic article so that the tinted article has a neutral gray or brown color in the excited state, is made by fusing at least two non-identical photochromic sections to an aromatic structure. The photochromic sections are selected so that the different absorption wavelengths of the excited photochromic sections give rise to a neutral gray or brown color in the plastic material and are selected from the group consisting of oxazines and pyrans. At least one of the photochromic sections is not an indolino spiropyran. The aromatic structure to which the photochromic sections are fused is selected from the group consisting of benzene, biphenyl, naphthalene, anthracene and phenanthrene. The positions of fusion of the photochromic sections on the aromatic structure are directly adjacent to the oxygen atom of the pyran or the oxygen or nitrogen atom of the oxazine.

1 Claim, No Drawings

PHOTOCHROMIC COMPOUNDS

CROSS-REFERENCE TO RELATED APPLICATIONS

This application is a Divisional of application Ser. No. 09/259,053, filed Mar. 1, 1999 (now abandoned), which application is a continuation of application Ser. No. 08/888,540, filed on Jul. 7, 1997 (now abandoned), which application is a continuation of application Ser. No. 08/578,583, filed on Apr. 17, 1996 (now abandoned), which is a national stage entry of PCT/DE94/00737 filed Jun. 28, 1994.

TECHNICAL FIELD

The present invention relates to photochromic compounds.

Photochromic compounds of this type are, by way of illustration, pyrans like those described, i.a., in U.S. Pat. No. 5,066,818, PCT publication WO 92/09593 or U.S. Pat. No. 4,818,096 or oxazines like those described in the U.S. Pat. Nos. 3,578,602, 4,215,010 and 4,637,698.

Furthermore, benzols and naphthalenes which are linked via two condensed spiropyrans to indoline are known from FR-A-1.450.583 and FR-A-1.451.332 as well as systems in which two identical indolino-spirobenzopyrans are linked via phenyl-phenyl or phenyl-$CH_2$-phenyl bridges. Other syntheses with linked indoline-spiropyran units were conducted in the 1960s by NCR, Dayton, Ohio.

The known pyrans and oxazines each absorb light in a relatively narrow spectral range. As a result the objects, such as, by way of illustration, ophthalmic lenses or sun-protection roofs, which are tinted using one of these photochromic compounds, are tinted intensively, by way of illustration, blue. However, in a number of applications, it is desirable if the object tinted with the photochromic compound is of a neutral gray or brown color.

Presently, one makes do in that one uses two or more photochromic dyestuffs which absorb in different wavelength ranges. With regard to this, reference is made to EP-A-0 146 136 or EU-A-0 397 803.

This approach has, however, the disadvantage that the lightening and darkening behavior of the employed photochromic compounds have to be tuned exactly to each other. Otherwise, the tinted object will change color during lightening and/or darkening. Furthermore, the dyestuffs have to be introduced in a stoichiometric ratio tolerated within narrow limits.

DESCRIPTION OF THE INVENTION

The object of the present invention is to provide photochromic compounds which tint the object in an excited state neutrally gray or brown even if only one photochromic compound is applied into respectively onto a to-be-tinted object.

The molecules of the invented photochromic compounds contain at least two photochromic sections, which are not indolino-spiropyrans and which are not identical and absorb in different wavelength ranges. In particular, the absorption wavelengths of the excited sections can be selected in such a manner that the compound is of a neutral gray or brown color.

It is particularly preferred if the molecules of the invented photochromic compounds contain two or more photochromic pyran units, oxazine units or pyran and oxazine units. In this instance, it is especially advantageous if the photochromic sections are 2H-pyrans and/or spirooxazines. In principle, known pyrans and oxazines can be employed as pyran units and oxazine units.

The invented molecules having 2H-pyrans and/or spirooxazines notably have the characteristic that they absorb, due to their high-condensed ring systems, in the longer wave range than the single systems according to the state of the art.

As consequently the UV section in the longer wave range of the sun irradiation, which is simultaneously more intensive, can be utilized for exciting substantially more intensive is dark tinting, e.g. for sunglasses, can be achieved with the same dyestuff concentration.

DESCRIPTION OF PREFERRED EMBODIMENTS

In the following, the structure of the invented compounds is described by way of example.

Several paths are possible for the synthesis of the invented compounds. These paths are shown in the following diagrams by way of example and reference is explicitly made to them for the explanation of all details not made apparent herein:

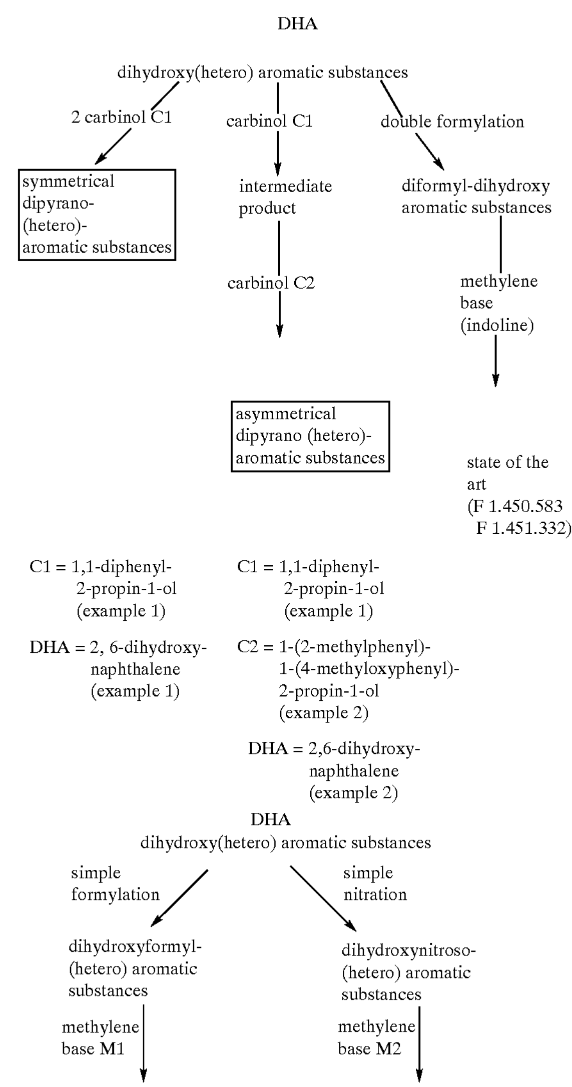

-continued

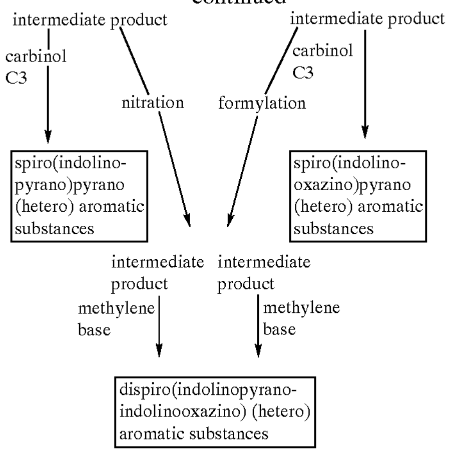

DHA = 2,6-dihydroxy-naphthalene

M1 = 1,3,3,3,4,7-penta methyl-2-methylene indoline

C3 = 1-cyclohexane-1-phenyl-2-propin-1-ol (example 3)

DHA = 2,6-dihydroxy-anthracene

M2 = 1,3,3-trimethyl-2-methylene indoline

C3 = 1-cyclohexane-1-phenyl-2-propin-1-ol (example 3)

DHA

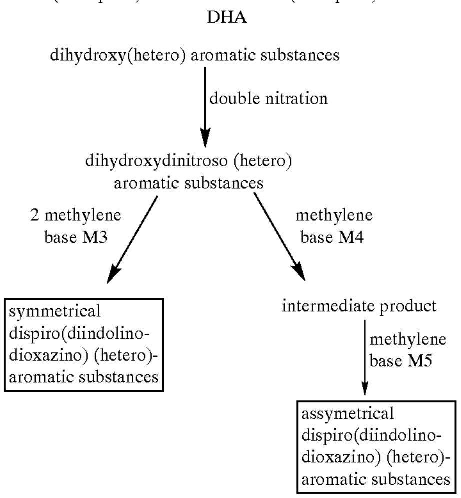

DHA = 2,6-dihydroxy-anthracene

M3 = 1-methyl-2-methylene-3-spiro cyclohexylindoline

DHA = 2,6-dihydroxy-anthracene

M4 = 5-nitro-1,3,3-trimethyl-2-methylene-indoline

M5 = 5-methoxyl-1,3,3-trimethyl-2-methylene-indoline

The invented compounds can be obtained, by way of illustration, by means of condensation of substituted polyhydroxy aromatic substances with the corresponding reactants in successive steps, in the case of symmetrical products partially even in one step.

The synthesis paths described here should only serve as examples. 2,3,; 1,6- and 2,7-dihydroxynaphthaline can be utilized with good exploitation. Likewise, other polyhyroxy aromatic substances, derivatives of benzols, anthracenes, phenanthrenes can be employed.

All of them can, in addition, carry other functional groups. Important is only that at least two hydroxy groups of the molecule possess each at least one free ortho-position. In paths which include nitration or transposition, only the para-position to the hydroxy group has to be occupied by Cl or Br.

Suited as reactants in the instance of acetylides are, in addition to diphenylcarbinol acetylides, corresponding compounds in which both phenyl rings are rigidly linked, by way of illustration, fluorene derivatives or anthracene derivatives. Non-aromatic acetylides, such as norboranes or adamantanes, can be used. In the case of methylene bases, all the methylene-group-containing systems and spiro-linking systems can be employed, by way of illustration, 2-methylene indolines, 2-methylene benzooxazoles, 2-methylene benzothiazoles, etc. If they are utilized in their salt forms, at least molar amounts of condensers have to be used.

In the following, the synthesis paths are described starting with dihydroxynaphthalenes. However, in principle, other aromatic substances, such as biphenylenes, anthracenes, phenanthrenes, etc. can be employed if they possess in their rings one or more all told at least 2 hydroxy groups having each at least one free ortho-position. The selection of the polyhydroxy aromatic substances as well as that of the reactants determine the features of the end product. If one employs 2,6-naphthalenediol as the starting product, pure dipyrano-naphthalenes can be obtained by transposition of initially only one hydroxy group with one acetylide, possibly isolation of the intermediate product and subsequent transposition with another acetylide. These absorb in the longer wave range than the monoproducts, in an excited state gold-orange to cinnabar red tones are obtained. By means of substituents, the color and in particular the lightening speed of the photochromic tinting are fixed. Alternatively, initially one aldehyde function is introduced in an ortho-position to a hydroxy group. The free hydroxy group is transposed with an acetylide, the salicyl-aldehyde group is then, after isolating the intermediate product, transposed with an active methyl group, by way of illustration with a so-called Fischer base. In this way, mixed spiro (indoline-pyrano)-pyrano-naphthalenes are obtained. On the other hand, if the ortho-positions of both hydroxy groups are provided with an aldehyde group, the compounds known from F 1.450.583 and F 1.481.322 are obtained by subsequent transposition with Fischer bases or indolinium salts. By transposing the salicylaldehyde group with a Fischer base, isolating the intermediate product, nitrating and subsequently transposing with another (also identical) Fischer base, mixed dispiro-(indoline-pyrano-indoline-oxazino)-naphthalenes are obtained. In a corresponding manner of proceeding, the preliminary product can be nitrated and both groups can be subsequently transposed together with indoline derivatives or both groups can be transposed in succession according to their different reactivity. Mononitrating the diol, subsequent transposition with, e.g. a Fischer base, isolating the intermediate product and transposing with an acetylide carbinol yield mixed spiro (indoline-oxazino)-pyrano-naphthalenes. Double nitrating and subsequent simultaneous or successive transposition with one (or various) indoline derivates yields dispiro (indoline-oxazino)-naphthalenes.

Analogously, other naphthalene diols, in particular, 2,7-, 2,3-, 1,5- and 1,6-dihydroxynaphtalene and 2,6-dihydroxyanthracene can be transposed to molecules containing two photochromic units. For the two photochromic sections, the known properties of the single systems apply. By way of illustration, using hydroxy functions in the 1,4,5 or 8-position of the naphthalene or the anthracene yields compounds which in an excited state absorb approximately 30 nm in a longer wave range and lighten distinctly slower than the 2,3,6 or 7-hydroxy aromatic substances. Likewise, the known reduction of the speed of lightening known from U.S. Pat. No. 5,066,818 applies in substitution of the aryl substituents (in the 2-position of the pyran ring) in the ortho-position for linking or the bathochromic shift of the photochromic color in the substitution of the naphthalene system in the 3-position or in the 6-position (U.S. Pat. No. 5,238, 981). In the same manner, the advantages of the spiro-(indoline-)naphthoxazine substituted in the 3-position of the naphthalene ring (WO 92/09593) are retained.

Compared to these compounds known from the state of the art, in an non-excited state there is a bathochromic absorption shift. At the same time, the extinction coefficient of the absorption of the longest wave rises. By this means, by way of illustration, in the case of dipyrano-systems, considerably improved efficiency is yielded compared to a mixture of single components, when irradiated with natural sunlight.

EXAMPLE 1

Syntheses a) Production of Carbinol 1:

54.7 g (0.30 mol) of benzophenone are dissolved in 150 ml of dry dimethyl sulfoxide, dripped into this solution while stirring are 27.6 g (0.30 mol) of lithium acetylide ethylene diamine complex. The solution turns dark yellow, with a fine, lighter precipitation occurring. The mixture is stirred for another 16 hours at room temperature. The orange-yellow suspension is poured on 750 g of crushed ice and immediately acidified with 2 n of HCl. The light ochre-colored suspension is shook out with ether until the precipitation depositing at the interphase is completely dissolved in the ether. The unified ether extracts are dried and filtered with $Na_2SO_4$. The ether is removed from the filtrate in the rotary evaporator. Left are 55.2 g of an orange oil that crystallizes out over night. It is characterized as 1,1 diphenyl-2-propin-1-ol by means of NMR data.

b) Production of Carbinol 2:

64 g (0.48 mol) of waterless aluminium chloride are suspended in 160 ml of dry 1,2-dichloroethane while stirring, then 65 g (0.42) of o-toluyl acid chloride are dripped into it at below 20° C. With dissolution of the Al compound, the suspension turns darker. Subsequently 43.2 g (0.40 mol) of anisol are dripped into it at still under 20° C. The solution turns dark brown, is stirred for another 1 hour at room temperature and left to rest for 15 hours. It is carefully poured onto 300 g of crushed ice, slightly acidified with 6 n of HCl and the organic phase is separated in a separating funnel. It is shook out several times with a 2% NaOH solution, dried over sodium sulfate and filtered. After removing the solvent, 70.2 g of an orange oil remain. Recrystallized from ether/hexane, the compound is identified as 2-methyl-4'-methoxy-benzophenone. This is dissolved in 150 ml of dry dimethylsulfide, into the light orange solution, 28.5 g (0.31 mol) of lithium acetylide ethylene diamine complex are dripped while stirring. The solution turns darker. The dark brown suspension is processed as under a) and 76.9 of a dark orange oil are yielded. NMR analysis of the compound recrystallized from pentane/ether confirms that the substance is 1-(2-methylphenyl)-1-(4-methoxyphenyl)-2-propin-1-ol.

c) Synthesis of the Asymmetrical Photochromic Compound:

Added to 16.0 g (0.10 mol) of 2,6-dihydroxynaphthalene in 150 ml of toluol, is a spatula tip of toluol-4-sulfonic acid. Into this, 20.8 g (0.10 mol) of carbinol 1 in 40 ml of toluol are dripped at room temperature, the solution immediately turning dark and showing orange-red photochromy. It is heated to 60° C. and still stirred for another 1 hour. Into this solution are dripped 25.2 g (0.10 mol) of carbinol 2 in 60 ml of toluol. The solution turns even darker, showing carmine red photochromy. The temperature is maintained at 60° C. for another 30 minutes. After cooling, in order to remove the not converted starting product, it is shook out twice with 300 ml of 5% NaOH. The separated organic phase is dried over sodium sulfate and filtered. The toluol is removed from the filtrate in the rotary evaporator. The residue is absorbed with methylene chloride and chromatographed with aluminium oxide. The first fraction, showing red photochromy, is collected. After removing the flow agent, 28.6 g of a dark red oil is yielded. This can be separated by means of another chromatography with toluol/hexane into the 2 symmetric and the desired product, which possesses a somewhat higher retention time. By recrystallization from ether/hexane, 16.3 g of weak yellowish crystals are yielded. The substance is identified as 2,2-diphenyl-8-(2-methylphenyl)-8-(4-methoxyphenyl)-dioxa(1,7)chrysene by means of NMR data.

EXAMPLE 2 a) Production of Carbinol 3:

50 g (0.265 mol) of benzoyl cyclohexane are dissolved in 150 ml of dry dimethyl sulfoxide, into the amber solution, 24.4 g (0.265 mol) of lithium acetylide ethylene diamine complex are dripped while stirring. The solution turns dark brown while depositing a fine precipitation. The mixture is stirred at room temperature for another 16 hours. Reprocessing like under a) yields 57.9 g of an orange-brown oil, which recrystallizes overnight into a yellow solid material. The NMR analysis confirms that the substance is 1-cyclohexane-1-phenyl-2-propin-1-ol.

Production of the Polymer Samples:

As the invented compounds were developed in particular for use in plastic materials, especially for use in ophthalmic lenses, their behavior is of decisive significance in these matrices. Due to their different structure, relative density and polarity, the invented substances and the cor responding compounds of the state of the art demonstrate varying diffusion behavior respectively migration behavior in the tinting of plastic materials according to the conventional processes of surface tinting (cf.). Moreover, the precise concentration of the dyestuff in the plastic material cannot be provided, thus no relationship can be constructed between the compounds and their absorption intensity, respectively their molar extinction coefficients. For this reason, another procedure for photochromic tinting of plastic materials which does not have these drawbacks is drawn upon for comparison.

It is described, by way of example, in EP-A-0227337. In this instance, a commercially available monomer (TS-150, Tokuyama Soda) is charged in each case with 500 ppm of the photochromic compound, poured into 2 mm plane glass forms and polymerized according to the production instructions. These samples are measured in a high-resolution spectral photometer (Lambda 9, Perkin Elmer). With the polymer containing the asymmetrical photochromic compound of example 1, the absorption band in the longest wave range and its very high intensity is striking due to its bathochromic shift.

What is claimed is:

1. A method for producing a photochromic compound suitable for use as a single substance for photochromic tinting of a transparent article made of a plastic material, said tinted article having a neutral gray or brown color in the excited state, the method comprising the step of fusing at least two non-identical photochromic sections that are selected so that the different absorption wavelengths of the excited photochromic sections give rise to a neutral gray or brown color in the plastic material, and which photochromic sections are further selected from the group consisting of oxazines and pyrans and of which at least one is not an indolino spiropyran, to an aromatic structure selected from the group consisting of benzene, biphenyl, naphthalene, anthracene and phenanthrene, the positions of fusion on the aromatic structure being directly adjacent to the oxygen atom of the pyran or the oxygen or nitrogen atom of the oxazine.

* * * * *